US006172090B1

(12) United States Patent
Ikeda et al.

(10) Patent No.: US 6,172,090 B1
(45) Date of Patent: Jan. 9, 2001

(54) PHARMACEUTICAL COMPOSITION

(75) Inventors: Hitoshi Ikeda, Higashiosaka; Takashi Sohda, Takatsuki; Hiroyuki Odaka, Kobe, all of (JP)

(73) Assignee: Takeda Chemical Industries, Ltd., Osaka (JP)

( * ) Notice: Under 35 U.S.C. 154(b), the term of this patent shall be extended for 0 days.

(21) Appl. No.: 09/303,495

(22) Filed: Apr. 30, 1999

Related U.S. Application Data

(62) Division of application No. 09/057,465, filed on Apr. 9, 1998, now Pat. No. 5,965,584, which is a division of application No. 08/667,979, filed on Jun. 19, 1996, now Pat. No. 5,952,356.

(30) Foreign Application Priority Data

Jun. 20, 1995 (JP) .................................................. 7-153500

(51) Int. Cl.$^7$ ........................ A61K 31/44; A61K 31/425; A61K 31/42; A61K 31/155

(52) U.S. Cl. .......................... 514/342; 514/369; 514/376; 514/635; 514/866

(58) Field of Search .................................... 514/342, 369, 514/376, 635, 866

(56) References Cited

U.S. PATENT DOCUMENTS

| 4,895,862 | 1/1990 | Alessi et al. ........................... 514/360 |
| 5,068,342 | 11/1991 | Zask et al. ............................. 548/183 |
| 5,859,037 | * 1/1999 | Whitcomb ............................. 514/369 |
| 5,952,356 | * 9/1999 | Ikeda et al. ........................... 514/340 |
| 5,965,584 | * 10/1999 | Ikeda et al. ........................... 514/342 |

FOREIGN PATENT DOCUMENTS

| 0 008 203 | 2/1980 | (EP) . |
| 0 193 256 | 9/1986 | (EP) . |
| 0 710 659 | 5/1996 | (EP) . |
| 4-66579 | 3/1992 | (JP) . |
| 4-69383 | 3/1992 | (JP) . |
| 5-202042 | 8/1993 | (JP) . |
| 93/03724 | 3/1993 | (WO) . |

OTHER PUBLICATIONS

M. Tominaga et al. "Thiazolidinediones (AD–4833 and CS–045) Improve Hepatic Insulin Resistance in Streptozotocin–Induced Diabetic Rats", Endocrine Journal, vol. 40, No. 3, pp. 345–349, 1993.

C. Hofmann et al., "Glucose Transport Deficiency in Diabetic Animals is Corrected by Treatment with the Oral Antihyperglycemic Agent Pioglitazone", Endocrinology, vol. 129, No. 4, pp. 1915–1925, 1991.

J. Karam, "Type II Diabetes and Syndrome X",Endocrinology and Metabolism Clinics of North America, vol. 21, No. 2, pp. 329–350, 1992.

S. Suter et al., "Metabolic Effects of New Oral Hypoglycemic Agent CS–045 in NIDDM Subjects", Diabetes Care, vol. 15, No. 2, pp. 193–203, 1992.

T. Toyoda, Iyaku Journal, vol. 30, No. 4, pp. 1130–1134, 1994.

Y. Sugiyama et al., "Effects of Pioglitazone on Glucose and Lipid Metabolism in Wistar Fatty Rats", Arzneim–Forsch/Drug Res., vol. 40, No. 1, pp. 263–267, 1990.

Ishida et al., "Oral Hypoglycemic Agents—New Oral Drugs and New Strategy of Treatment", Clinic All–round, vol. 43, pp. 2615–2521, 1994 (and English translation).

Medicine and Drug Journal, vol. 30, No. 4 (Japanese) with partial English translation).

Therapeutic Research, 14 (No. 10), 4122 to 4126 (1993) (and English translation).

Clinic and Medicine, 9 (Suppl. 3), 19 to 37 (1993).

Clinic and Medicine, 9 (Suppl. 3), 39 to 60 (1993).

Recent Medicine, 33 197 (1982).

J. Sturis et al., "Prevention of Diabetes Does Not Completely Prevent Insulin Secretory Defects in the ZDF rat", vol. 169, No. 4, pp. 786–792, Oct., 1995.

Z. Bloomgarden, "American Diabetes Association Scientific Sessions, 1995", The Journal of Clinical and Applied Research and Education, vol. 18, No. 8, pp. 1215–1219, Aug., 1995.

R. Whitcomb et al., "Thiazolidinediones", Expert Opinion on Investigational Drugs, vol. 4, No. 12, pp. 1299–1309, Dec., 1995.

K. Nihalani et al., "Newer Oral Hypoglyceamic (Antidiabetic) Agents", Journal of the Diabetic Association of India, vol. 34, Nos. 3 & 4, 1994.

Sugiyama et al., "Effects of Pioglitazone on Hepatic and Peripheral Insulin Resistance in Wistar Fatty Rats," Arzneim.–Forsch., vol. 40, pp. 436–440 (Apr. 1990).

Ikeda et al., "Effects of Pioglitazone on Glucose and Lipid Metabolism in Normal and Insulin Resistant Animals," Arzneim.–Forsch., vol. 40, pp. 156–162 (Feb. 1990).

Hofmann et al., "New Oral Thiazolidinedione Antidiabetic Agents Act as Insulin Sensitizers," Diabetes Care, vol. 15, pp. 1075–1078 (Aug. 1992).

Hofmann et al., "Treatment of Insulin–Resistant Mice with the Oral Antidiabetic Agent Pioglitazone: Evaluation of Liver GLUT2 and Phosphoenolpyruvate Carboxykinase Expression," Endocrinology, vol. 130, pp. 735–740 (Feb. 1992).

(List continued on next page.)

Primary Examiner—Kevin E. Weddington
(74) Attorney, Agent, or Firm—Wenderoth, Lind & Ponack, LLP.

(57) ABSTRACT

Pharmaceutical composition which comprises an insulin sensitivity enhancer in combination with other antidiabetics differing from the enhancer in the mechanism of action, which shows a potent depressive effect on diabetic hyperglycemia and is useful for prophylaxis and treatment of diabetes.

17 Claims, No Drawings

OTHER PUBLICATIONS

Iwanishi et al., "Effect of Pioglitazone on Insulin Receptors of Skeletal Muscles from High Fat–Fed Rats," Metabolism, vol. 42, pp. 1017–1021 (Aug. 1993).

Iwanishi et al., "New Oral Agent to Increase Insulin Sensitivity by Activating Kinase Activity of Insulin Receptors," Diabetes, vol. 39, abstract 474 (Jun. 1990).

Kobayashi et al., "Pioglitazone Increases Insulin Sensitivity by Activating Insulin Receptor Kinase," Diabetes, vol. 41, pp. 476–483 (Apr. 1992).

Hofmann et al., "Insulin Sensitization in Diabetic Rat Liver by an Antihyperglycemic Agent," Metabolism, vol. 44, pp. 384–389 (Mar. 1995).

de Souza et al., "Insulin Secretory Defect in Zucker fa/fa Rats is Improved by Ameliorating Insulin Resistance," Diabetes, vol. 44, pp. 984–991 (Aug. 1995).

Hofmann et al., "Glucose Transport Deficiency in Diabetic Animals is Corrected by Treatment with the Oral Antihyperglycemic Agent Pioglitazone," Endocrinology, vol. 129, pp. 1915–1925 (Mar. 1991).

Colca et al., "Antihyperglycaemic Thiazolidinediones: Ciglitazone and its Analogues," New Antidiabetic Drugs, pp. 255–261 (1990).

Tominaga et al., "Thiazolidinediones (AD–4833 and CS–045) Improve Hepatic Insulin Resistance in Streptozotocin–Induced Diabetic Rats," Endocrine Journal, vol. 40, pp. 343–349 (Jun. 1993).

Weinstock et al., "Pioglitazone: In Vitro Effects on Rat Hepatoma Cells and in vivo Liver Hypertrophy in KKA$^y$ Mice," Pharmacology, vol. 54, pp. 169–178 (Apr. 1997).

El–Kebbi et al., "Regulation of Glucose Transport by Pioglitazone in BC3H–1 Myocytes," Clinical Research, vol. 39, p. 837A (Dec. 1991).

Kemnitz et al., "Pioglitazone Increases Insulin Sensitivity, Reduces Blood Glucose, Insulin, and Lipid Levels, and Lowers Blood Pressure in Obese, Insulin–Resistant Rhesus Monkeys," Diabetes, vol. 43, pp. 204–211 (Feb. 1994).

Meehan et al., "Pioglitazone Reduces Blood Pressure and Improves Insulin Sensitivity in Fructose–Fed Rats," Clinical Research, vol. 41, p. 21A (Feb. 1993).

Colca et al., "Pioglitazone Hydrochloride Inhibits Cholesterol Absorption and Lowers Plasma Cholesterol Concentrations in Cholesterol–Fed Rats," Diabetes, vol. 40, pp. 1669–1674 (Dec. 1991).

Sohda et al., "Studies on Antidabetic Agents, 11. Novel Thiazolidinedione Derivatives as Potent Hypoglycemic and Hypolipidemic Agents," Journal of Medicinal Chemistry, vol. 35, pp. 2617–2626 (Jul. 1992).

Sugiyama et al., "Pathogenesis Hyperglycemia in Genetically Obese–Hyperglycemic Rats, Wistar Fatty: Presence of Hepatic Insulin Resistance," Endocrinologia Japonica, vol. 36, pp. 65–73 (Feb. 1989).

Suter et al., "Metabolic Effects of New Oral Hypoglycemic Agent CS–045 in NIDDM Subjects," Diabetes Care, vol. 15, pp. 193–203 (Feb. 1992).

Iwamoto et al., "Effect of New Oral Antidiabetic Agent CS–045 on Glucose Tolerance and Insulin Secretion in Patients with NIDDM," Diabetes Care, vol. 14, pp. 1083–1086 (Nov. 1991).

Norris et al. Comparison of Troglitazone (C1991) Dosing Regimens and Placebo in the Treatment of Patients with NIDDM, Diabetes, vol. 42, Supp. 1, Abstract 188 (Jun. 1993).

Fukuda et al., "Results of a Pilot Study in which Troglitazone and Insulin were Jointly Administered to NIDDM Patients," Journal of Clinical Therapeutics & Medicines, vol. 11, pp. 2055–2062 (Oct. 1995) (with translation, based on abstract published at 15th Diabetes Fed. Cong., Nov. 6–11, 1994, Kobe).

Kanazawa, "Agent for Lowering Insulin Resistance— CS–045," Diabetes Frontier, vol. 3, pp. 570–574 (1992).

Onuma et al., "The Effect of a New Oral Hypoglycemic Drug, CS–045, on Glucose Tolerance and Serum Lipids in Nonobese Japanese Patients with Non–Insulin–Dependent Diabetes Mellitus: A Pilot Study," Current Therapeutic Research, vol. 55, pp. 416–421 (Apr. 1994).

Kuzuya et al., "A Pilot Clinical Trial of a New Oral Hypoglycemic Agent, CS–045, in Patients with Non–Insulin Dependent Diabetes Mellitus," Diabetes Research and Clinical Practice, vol. 11, pp. 147–154 (1991).

Takino et al., "Increased Insulin Responsiveness After CS–045 Treatment in Diabetes Associated with Werner's Syndrome," Diabetes Research and Clinical Practice, vol. 24, pp. 167–172 (Jul. 1994).

Fujiwara et al., "Characterization on New Oral Antidiabetic Agent CS–045," Diabetes, vol. 37, pp. 1549–1558 (Sep. 1988).

Lee et al., "Metabolic Effects of Troglitazone on Fructose–Induced Insulin Resistance in the Rat," Diabetes, vol. 43, pp. 1435–1439 (Dec. 1994).

Khoursheed et al., "Metabolic Effects of Troglitazone on Fat–Induced Insulin Resistance in the Rat," Metabolism, vol. 44, pp. 1489–1494 (Nov. 1995).

Valiquette et al., "Troglitazone Dose–Response Study in Patients with Noninsulin Dependent Diabetes," Clinical Research, vol. 42, p. 400A (Oct. 1994).

Nolan et al., "Improvement in Glucose Tolerance and Insulin Resistance in Obese Subjects Treated with Troglitazone," The New England Journal of Medicine, vol. 331, pp. 1188–1193 (Nov. 1994).

Ciaraldi et al., "In Vitro Studies on the Action of CS–045, a New Antidiabetic Agent," Metabolism, vol. 39, pp. 1056–1062 (Oct. 1990).

Oakes et al., A New Antidiabetic Agent, BRL 49653, Reduces Lipid Availability and Improves Insulin Action and Glucoregulation in the Rats, Diabetes, vol. 43, pp. 1203–1210 (Oct. 1994).

Eldershaw et al., "Treatment with the Thiazolidinedione (BRL 49653) Decreases Insulin Resistance in Obese Zucker Hindlimb," Hormone and Metabolic Research, vol. 27, pp. 169–172 (Apr. 1995).

Cawthorne et al., "Anti–Hyperglycaemic Efficacy of BRL–49653, a Highly Potent Thiazolidinedione, in Animal Models of Non–Insulin Dependent Diabetes," Diabetes, vol. 42, Supp. 1, Abstract 654 (Jun. 1993).

Kraegen et al., "Effects of BRL 49653 in Normal and Insulin Resistant (High–Fat–Fed) Rats; New Information on the Mode of Action of Thiazolidinediones," Diabetes, vol. 42, Supp. 1, Abstract 257 (Jun. 1993).

Smith et al., "BRL 49653 Normalises Glycaemic Control in Zucker fa/fa Rats by Improving Hepatic and Peripheral Tissue Sensitivity to Insulin," Diabetologia, vol. 36, Abstract 707 (Aug. 1993).

Young et al., "Chronic Treatment of OB/OB Mice with BRL 49653 Enhances Insulin–Stimulated Translocation of GLUT–4 to the Adipocyte Cell Surface," Diabetologia, vol. 36, Abstract 285 (Aug. 1993).

Young et al., "Repeat Treatment of Obese Mice with BRL 49653, a New and Potent Insulin Sensitizer, Enhances Insulin Action in White Adipocytes," Diabetes, vol. 44, pp. 1087–1092 (Sep. 1995).

Fujita et al., "Reduction of Insulin Resistance in Obese and/or Diabetic Animals by 5–[4–(1–Methylcyclohexyl-methoxy)benzyl]–Thiazolidine–2, 4–Dione (ADD–3878, U–63,287 Ciglitazone), a New Antidabetic Agent," Diabetes, vol. 32, pp. 804–810 (Sep. 1983).

Diani et al., "Ciglitazone, a New Hypoglycaemic Agent. 4. Effect on Pancreatic Islet of C57BL/6J–ob/ob and C57BL/KsJ–db/db Mice," Diabetologia, vol. 27 (Aug. 1984).

Stevenson et al., "Actions of Novel Antidiabetic Agent Englitazone in Hyperglycemic Hyperinsulinemic ob/ob Mice," Diabetes, vol. 39, pp. 1218–1227 (Oct. 1990).

Adams et al., "Effects of the Antidiabetic Agent Englitazone on Hepatic Gluconeogenesis and Glycosis," FASEB Journal, vol. 9, Abstract 5800 (Apr. 1995).

Clark et al., "Englitazone Sodium," Drugs of the Future, vol. 17, pp. 182–184 (Mar. 1992).

Yoshioka et al., Tonyobyou (Diabetes), vol. 34, Supplement 1 (1991) item H320 (with English translation).

Sakamoto et al., Tonyobyou (Diabetes), vol. 36, Supplement 1 (1993) item 3Q08 (with English translation).

Tanaka et al., Tonyobyou (Diabetes), vol. 37, No. 2 (1994) item 6 (with English translation).

Iwamoto et al., Tonyobyou (Diabetes), vol. 38, Supplement 1 (1995) item 2159 (with English translation).

The Pink Sheet, vol. 57, Issue 16, Re: FDC Accession No. 00570160005, Apr. 17, 1995.

Martindale, The Extra Pharmacopoeia, Thirtieth Edition, Edited by Reynolds, James E.F., *The Pharmaceutical Press*, London, pp. 276–291, 1993.

Foot, E.A. et al., "Improved Metabolic Control by Addition of Troglitazome to Glibenclamide Therapy in Non–Insulin–Dependent Diabetics", *31st Annual Meeting of the European Association for the Study of Diabetes*, Stockholm, Sweden, Sep. 12–16, 1995 (abstract only).

N. Hotta, Diabetes Update, No. 10, Kashikojima Seminar, pp. 68–77 (1994), with English translation.

H. Lebovitz, Diabetes Care, vol. 17, No. 12, pp. 1542–1544 (1994).

N. Hotta, Chronic Diabetes, vol. 6, No. 1, pp. 98–102 (1995).

G. Williams, The Lancet, vol. 343, pp. 95–100 (1994).

J. Lehman et al., The Journal of Biological Chemistry, vol. 270, No. 22, pp. 12953–12956 (1995).

R. Jackson et al., Diabetes, vol. 36, pp. 632–639 (1987).

R. Donnelly et al., Br. J. Clin. Pharmac., vol. 37, pp. 311–320 (1994).

Akanuma et al., J. Clinical Therapeutics & Medicines, 9 Suppl. 3, pp. 19–37 (1993) (English translation).

Akanuma et al., J. Clinical Therapeutics & Medicines, 9 Suppl. 3, pp. 36–60 (1993) (English translation).

J. Clinical Therapeutics and Medicines, 9, Suppl. 3, 151–164 (1993) with translation.

* cited by examiner

PHARMACEUTICAL COMPOSITION

This is a divisional application of Ser. No. 09/057,465, filed Apr. 9, 1998, U.S. Pat. No. 5,965,584 which was a divisional application of Ser. No. 08/667,979, filed Jun. 19, 1996 now U.S. Pat. No. 5,956,356.

BACKGROUND OF THE INVENTION

1. Field of the Invention

The present invention relates to a pharmaceutical composition comprising an insulin sensitivity enhancer in combination with one or more other antidiabetics differing from said enhancer in the mechanism of action.

2. Description of Related Art

Recent years, the pathology of diabetes has become more and more understood and, in parallel, drugs specific for the respective pathologic states have been developed. Accordingly a variety of drugs having new mechanism of action have appeared one after another.

Insulin sensitivity enhancers are also known as insulin resistance deblockers because they have the action to normalize the impaired insulin receptor function, and are gathering much attention in these years.

Regarding such insulin sensitivity enhancers, a very useful compound such as pioglitazone has been developed [Fujita et al., Diabetes 32, 804–810, 1983, JP-A S55(1980)-22636 (EP-A 8203), JP-A S61(1986)-267580 (EP-A 193256)]. Pioglitazone restores the impaired insulin receptor function to normalize the uneven distribution of glucose transporters in cells, the cardinal enzyme systems associated with glycometabolism, such as glucokinase, and enzyme systems associated with lipidmetabolism, such as lipoprotein lipase. As the results, insulin resistance are deblocked to improve glucose tolerance, and lower the plasma concentrations of neutral lipids and free fatty acids. Since these actions of pioglitazone are comparatively gradual and the risk of side effect in long-term administration is also low, this compound is useful for obese patients who are presumed to be highly insulin-resistant.

Also, insulin sensitivity enhancers such as CS-045, thazolidinedione derivatives and substituted thiazolidinedione derivatives are reported to be used in combination with insulin [JP-A H4(1992)-66579, JP-A H4(1992)-69383, JP-A H5(1993)-202042]. However, the pharmaceutical composition having a specific combination of the present invention is unknown.

Diabetes is a chronic disease with diverse pathologic manifestations and is accompanied by lipidmetabolism disorders and circulatory disorders as well as glycometabolism disorders. As the results, diabetes tends to progress entailing various complications in many cases. Therefore, it is necessary to select the drug of choice for the prevailing disease state in each individual case. However, this selection is often difficult in clinical settings because single use of each individual drug can not bring sufficient effects in some disease states and there are various problems such as side effect which is caused by an increased dose or a long-term administration.

SUMMARY OF THE INVENTION

In view of the above state of the art, the inventors of the present invention did much research to develop antidiabetics which would not virtually cause adverse reactions even on long-term administration and could be effective for a large cohort of the diabetic population. As a consequence, they discovered that the above object can be accomplished by using an insulin sensitivity enhancer, such as the drug described above, in combination with other antidiabetics differing from said enhancer in the mechanism of action, and accordingly have perfected the present invention.

The present invention, therefore, relates to:

1) Pharmaceutical composition which comprises an insulin sensitivity enhancer in combination with at least one member of the group consisting of an α-glucosidase inhibitor, an aldose reductase inhibitor, a biguanide, a statin compound, a squalene synthesis inhibitor, a fibrate compound, a LDL catabolism enhancer and an angiotensin converting enzyme inhibitor;

2) Pharmaceutical composition according to 1), wherein the insulin sensitivity enhancer is a compound represented by the formula:

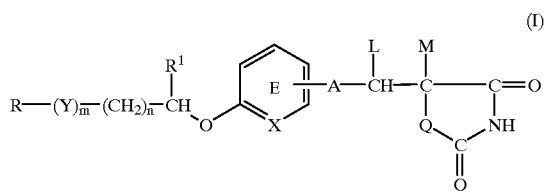

wherein R represents an optionally substituted hydrocarbon or heterocyclic group; Y represents a group represented by —CO—, —CH(OH)— or —NR$^3$— (wherein R$^3$ represents an optionally substituted alkyl group); m is 0 or 1; n is 0, 1 or 2; X represents CH or N; A represents a bond or a $C_{1-7}$ divalent aliphatic hydrocarbon group; Q represents oxygen atom or sulfur atom; R$^1$ represents hydrogen atom or an alkyl group; ring E may optionally have 1 to 4 substituents, and the substituents may optionally be combined with R$^1$ to form a ring; L and M respectively represent hydrogen atom, or L and M may optionally be combined with each other to form a bond; or a pharmacologically acceptable salt thereof;

3) Pharmaceutical composition according to 2), wherein the compound represented by the formula (I) is pioglitazone;

4) Pharmaceutical composition according to 1), which comprises an insulin sensitivity enhancer in combination with an α-glucosidase inhibitor;

5) Pharmaceutical composition according to 4), wherein the α-glucosidase inhibitor is voglibose;

6) Pharmaceutical composition according to 4), wherein the insulin sensitivity enhancer is pioglitazone and the α-glucosidase inhibitor is voglibose;

7) Pharmaceutical composition according to 1), which is for prophylaxis or treatment of diabetes;

8) Pharmaceutical composition which comprises a compound represented by the formula:

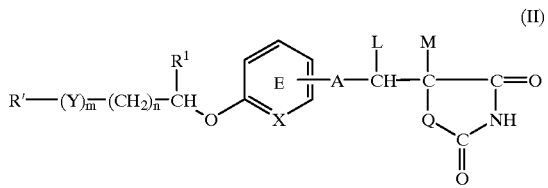

wherein R' represents an optionally substituted hydrocarbon or heterocyclic group; Y represents a group represented by —CO—, —CH(OH)— or —NR³— (wherein R³ represents an optionally substituted alkyl group); m is 0 or 1; n is 0, 1 or 2; X represents CH or N; A represents a bond or a $C_{1-7}$ divalent aliphatic hydrocarbon group; Q represents oxygen atom or sulfur atom; $R^1$ represents hydrogen atom or an alkyl group; ring E may optionally have 1 to 4 substituents, and the substituents may optionally be combined with $R^1$ to form a ring; L and M respectively represent hydrogen atom, or L and M may optionally be combined with each other to form a bond; with a proviso that R' does not represent benzopyranyl group when m and n are 0, X represents CH, A represents a bond, Q represents sulfur atom, $R^1$, L and M represent hydrogen atom and ring E does not have further substituents; or a pharmacologically acceptable salt thereof in combination with an insulin secretion enhancer and/or an insulin preparation;

9) Pharmaceutical composition according to 8), wherein the compound represented by the formula (II) is the compound represented by the formula:

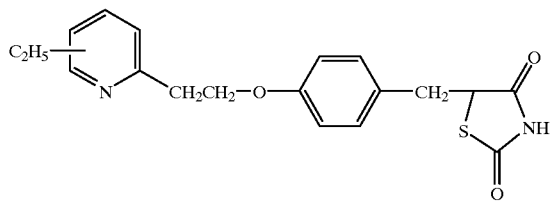

(III)

10) Pharmaceutical composition according to 8), wherein the compound represented by the formula (II) is pioglitazone;

11) Pharmaceutical composition according to 8), wherein the insulin secretion enhancer is glibenclamide;

12) Pharmaceutical composition according to 8), wherein the compound represented by the formula (II) is pioglitazone and the insulin secretion enhancer is glibenclamide;

13) Pharmaceutical composition according to 8), which is for prophylaxis or treatment of diabetes.

DETAILED DESCRIPTION OF THE INVENTION

The term "insulin sensitivity enhancer" as used in this specification means any and all drug substances that restore the impaired insulin receptor function to deblock insulin resistance and consequently enhance insulin sensitivity. As examples of the insulin sensitivity enhancer, the compound represented by the formula (I) or a pharmacologically acceptable salt thereof can be mentioned.

In the formula (I), as the hydrocarbon group in the optionally substituted hydrocarbon group represented by R, mention is made of aliphatic hydrocarbon groups, alicyclic hydrocarbon groups, alicyclic-aliphatic hydrocarbon groups, aromatic aliphatic hydrocarbon groups and aromatic hydrocarbon groups. Number of carbon atoms in these hydrocarbon groups is preferably 1 to 14.

The aliphatic hydrocarbon groups are preferably those having 1 to 8 carbon atoms. As the aliphatic hydrocarbon groups, mention is made of $C_{1-8}$ saturated aliphatic hydrocarbon groups (e.g. alkyl group) as exemplified by methyl, ethyl, propyl, isopropyl, butyl, isobutyl, sec.-butyl, t.-butyl, pentyl, isopentyl, neopentyl, t.-pentyl, hexyl, isohexyl, heptyl and octyl, and $C_{2-8}$ unsaturated aliphatic hydrocarbon groups (e.g. alkenyl group, alkadienyl group, alkynyl group, alkadiynyl group) as exemplified by vinyl, 1-propenyl, 2-propenyl, 1-butenyl, 2-butenyl, 3-butenyl, 2-methyl-1-propenyl; 1-pentenyl, 2-pentenyl, 3-pentenyl, 4-pentenyl; 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl.

The alicyclic hydrocarbon groups are preferably those having 3 to 7 carbon atoms. As the alicyclic hydrocarbon groups, mention is made of $C_{3-7}$ saturated alicyclic hydrocarbon groups (e.g. cycloalkyl group) as exemplified by cyclopropyl, cyclobutyl, cyclopentyl, cyclohexyl and cycloheptyl, and $C_{5-7}$ unsaturated alicyclic hydrocarbon groups (e.g. cycloalkenyl group, cycloalkadienyl group) as exemplified by 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl.

As the alicyclic-aliphatic hydrocarbon groups, mention is made of, among those formed by combination of the above-mentioned alicyclic hydrocarbon groups with aliphatic hydrocarbon groups (e.g. cycloalkyl-alkyl group, cycloalkenyl-alkyl group), ones having 4 to 9 carbon atoms as exemplified by cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3cyclohexenylmethyl, cyclohexylethyl, cyclohexylpropyl, cycloheptylmethyl and cycloheptylethyl.

The aromatic aliphatic hydrocarbon groups are preferably those having 7 to 13 carbon atoms (e.g. aralkyl group). As the aromatic aliphatic hydrocarbon groups, mention is made of $C_{7-9}$ phenylalkyl as exemplified by benzyl, phenethyl, 1-phenylethyl, 3-phenylpropyl, 2-phenylpropyl and 1-phenylpropyl, and $C_{11-13}$ naphthylalkyl as exemplified by α-naphthylmethyl, α-naphthylethyl, β-naphthylmethyl and β-naphthylethyl.

As the aromatic hydrocarbon groups, mention is made of, ones having 6 to 14 carbon atoms as exemplified by phenyl, naphthyl (α-naphtyl, β-naphthyl).

In the formula (I), as the heterocyclic group in the optionally substituted heterocyclic group represented by R, mention is made of, for example, 5- to 7-membered heterocyclic groups containing, as a ring component atom, 1 to 4 hetero atoms selected from oxygen atom, sulfur atom and nitrogen atom, and a condensed ring group. As the condensed ring, mention is made of, for example, these 5- to 7-membered heterocyclic groups condensed with 6-membered ring containing one or two nitrogen atoms, benzene ring or 5-membered ring containing one sulfur atom.

Examples of these heterocyclic groups include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-oxadiazol-5-yl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin- 2-yl, 1H-imidazo[4,5-b]pyrazin-2-yl and benzopyranyl. Among them, pyridyl, oxazolyl or thiazolyl group is preferable.

In the formula (I), the hydrocarbon group and heterocyclic group represented by R may optionally have 1 to 5, preferably 1 to 3 substituents at any substitutable positions. Examples of such substituents include aliphatic hydrocarbon group, alicyclic hydrocarbon group, aryl group, aromatic heterocyclic group, non-aromatic heterocyclic group, halogen atom, nitro group, optionally substituted amino group, optionally substituted acyl group, optionally substituted hydroxyl group, optionally substituted thiol group, optionally esterified carboxyl group, amidino group, carbamoyl group, sulfamoyl group, sulfo group, cyano group, azido group and nitroso group.

Examples of the aliphatic hydrocarbon groups include $C_{1-15}$ straight-chain or branched aliphatic hydrocarbon groups as exemplified by alkyl group, alkenyl group, and alkynyl group.

Preferable examples of the alkyl group include $C_{1-10}$ alkyl groups such as methyl, ethyl, propyl, isopropyl, butyl, isobutyl, sec.-butyl, t.-butyl, pentyl, isopentyl, neopentyl, t.-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl.

Preferable examples of the alkenyl group include $C_{2-10}$ alkenyl groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

Preferable examples of the alkynyl group include $C_{2-10}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

As the alicyclic hydrocarbon group, mention is made of $C_{3-12}$ saturated or unsaturated alicyclic hydrocarbon groups as exemplified by cycloalkyl group, cycloalkenyl group and cycloalkadienyl group.

Preferable examples of cycloalkyl group include $C_{3-10}$ cycloalkyl groups such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl.

Preferable examples of the cycloalkenyl group include $C_{3-10}$ cycloalkenyl groups such as 2-cyclopenten-1-yl, 3-cyclopenten-1-yl, 2-cyclohexen-1-yl and 3-cyclohexen-1-yl.

Preferable examples of the cycloalkadienyl group include $C_{4-10}$ cycloalkadienyl groups such as 2,4-cyclopentadien-1-yl, 2,4-cyclohexadien-1-yl and 2,5-cyclohexadien-1-yl.

Preferable examples of the aryl group include $C_{6-14}$ aryl groups such as phenyl, naphthyl (1-naphthyl, 2-naphthyl), anthryl, phenanthryl and acenaphthylenyl.

Preferable examples of the aromatic heterocyclic group include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl; and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

Preferable examples of the non-aromatic heterocyclic group include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, pyrrolidino, piperidino, morpholino and thiomorpholino.

Examples of the halogen atom include fluorine, chlorine, bromine and iodine.

As the substituted amino group in the optionally substituted amino group, mention is made of, N-monosubstituted amino group and N,N-disubstituted amino group. Examples of the substituted amino groups include amino groups having one or two substituents selected from $C_{1-10}$ alkyl group, $C_{2-10}$ alkenyl group, $C_{2-10}$ alkynyl group, aromatic group, heterocyclic group and $C_{1-10}$ acyl group (e.g. methylamino, dimethylamino, ethylamino, diethylamino, dibutylamino, diallylamino, cyclohexylamino, phenylamino, N-methyl-N-phenyl-amino, acetylamino, propionylamino, benzoylamino and nicotinoylamino).

As the acyl group, mention is made of $C_{1-13}$ acyl groups such as $C_{1-10}$ alkanoyl group, $C_{3-10}$ alkenoyl group, $C_{4-10}$ cycloalkanoyl group, $C_{4-10}$ cycloalkenoyl group and $C_{6-12}$ aromatic carbonyl group.

Preferable examples of the $C_{1-10}$ alkanoyl group include formyl acetyl, propionyl, butyryl, isobutyryl, valeryl, isovaleryl, pivaloyl, hexanoyl, heptanoyl and octanoyl. Preferable examples of the $C_{3-10}$ alkenoyl group include acryloyl, methacryloyl, crotonoyl and isocrotonoyl. Preferable examples of $C_{4-10}$ cycloalkanoyl group include cyclobutanecarbonyl, cyclopentanecarbonyl, cyclohexanecarbonyl and cycloheptanecarbonyl. Preferable examples of $C_{4-10}$ cycloalkenoyl group include 2-cyclohexenecarbonyl. Preferable examples of $C_{6-12}$ aromatic carbonyl group include benzoyl, naphthoyl and nicotinoyl.

As the substituent in the substituted acyl group, mention is made of, for example, $C_{1-3}$ alkyl group, $C_{1-3}$ alkoxy group, halogen atom (e.g. chlorine, fluorine, bromine, etc.), nitro group, hydroxyl group and amino group.

As the substituted hydroxyl group in the optionally substituted hydroxyl group, mention is made of, for example, alkoxy group, cycloalkyloxy group, alkenyloxy group, cycloalkenyloxy group, aralkyloxy group, acyloxy group and aryloxy group.

Preferable examples of the alkoxy group include $C_{1-10}$ alkoxy groups such as methoxy, ethoxy, propoxy, isopropoxy, butoxy, isobutoxy, sec.-butoxy, t.-butoxy, pentyloxy, isopentyloxy, neopentyloxy, hexyloxy, heptyloxy and nonyloxy. Preferable examples of the cycloalkyloxy group include $C_{3-10}$ cycloalkyloxy groups such as cyclobutoxy, cyclopentyloxy and cyclohexyloxy. Preferable examples of the alkenyloxy group include $C_{2-10}$ alkenyloxy groups such as allyloxy, crotyloxy, 2-pentenyloxy and 3-hexenyloxy. Preferable examples of the cycloalkenyloxy group include $C_{3-10}$ cycloalkenyloxy groups such as 2-cyclopentenyloxy and 2-cyclohexenyloxy. Preferable examples of the aralkyloxy group include $C_{7-10}$ aryloxy groups such as phenyl-$C_{1-4}$alkyloxy (e.g. benzyloxy and phenethyloxy). Preferable examples of the acyloxy group include $C_{2-13}$ acyloxy group, more preferably $C_{2-4}$ alkanoyloxy groups (e.g. acetyloxy, propionyloxy, butyryloxy and isobutyryloxy). Preferable examples of the aryloxy group include $C_{6-14}$ aryloxy groups such as phenoxy and naphthyloxy. The aryloxy group may optionally have one or two substituents such as halogen atom (e.g. chlorine, fluorine, bromine). Examples of the substituted aryloxy group include 4-chlorophenoxy.

As the substituted thiol group in the optionally substituted thiol group, mention is made of, alkylthio group, cycloalkylthio group, alkenylthio group, cycloalkenylthio group, aralkylthio group, acylthio group and arylthio group.

Preferable examples of the alkylthio group include $C_{1-10}$ alkylthio groups such as methylthio, ethylthio, propylthio, isopropylthio, butylthio, isobutylthio, sec.-butylthio, t.-butylthio, pentylthio, isopentylthio, neopentylthio, hexylthio, heptylthio and nonylthio. Preferable examples of the cycloalkylthio group include $C_{3-10}$ cycloalkylthio groups such as cyclobutylthio, cyclopentylthio and cyclohexylthio. Preferable examples of the alkenylthio group include $C_{2-10}$ alkenylthio groups such as allylthio, crotylthio, 2-pentenylthio and 3-hexenylthio. Preferable examples of the cycloalkenylthio group include $C_{3-10}$ cycloalkenylthio groups such as 2-cyclopentenylthio and 2-cyclohexenylthio. Preferable examples of the aralkylthio include $C_{7-10}$ aralkylthio groups such as phenyl-$C_{1-4}$alkylthio (e.g. benzylthio and phenethylthio). Preferable examples of the acylthio group include $C_{2-13}$ acylthio group, more preferably $C_{2-4}$ alkanoylthio groups (e.g. acetylthio, propionylthio, butyrylthio and isobutyrylthio).

Preferable examples of the arylthio group include $C_{6-14}$ arylthio groups such as phenylthio and naphthylthio. The arylthio group may optionally have one or two substituents such as halogen atom (e.g. chlorine, fluorine, bromine). Examples of the substituted arylthio group include 4-chlorophenylthio.

As the optionally esterified carboxyl group, mention is made of, for example, alkoxycarbonyl group, aralkyloxycarbonyl group and aryloxycarbonyl group.

Preferable examples of the alkoxycarbonyl group include $C_{2-5}$ alkoxycarbonyl groups such as methoxycarbonyl, ethoxycarbonyl, propoxycarbonyl and butoxycarbonyl. Preferable examples of the aralkyloxycarbonyl group include $C_{8-10}$ aralkyloxycarbonyl groups such as benzyloxycarbonyl. Preferable examples of the aryloxycarbonyl group include $C_{7-15}$ aryloxycarbonyl groups such as phenoxycarbonyl and p-tolyloxycarbonyl.

Among the substituents on the hydrocarbon group and heterocyclic group represented by R, $C_{1-10}$ alkyl groups, aromatic heterocyclic groups and $C_{6-14}$ aryl groups are preferable, and $C_{1-3}$ alkyl, furyl, thienyl, phenyl and naphthyl are especially preferable.

In the formula (I), substituents on the hydrocarbon group and heterocyclic group which are represented by R, may, when they are alicyclic hydrocarbon group, aryl group, aromatic heterocyclic group or non-aromatic heterocyclic group, have one or more, preferably 1 to 3, of suitable substituents respectively. Examples of these substituents include $C_{1-6}$ alkyl groups, $C_{2-6}$ alkenyl groups, $C_{2-6}$ alkynyl groups, $C_{3-7}$ cycloalkyl groups, $C_{6-14}$ aryl groups, aromatic heterocyclic groups (e.g. thienyl, furyl, pyridyl, oxazolyl and thiazolyl), non-aromatic heterocyclic groups (e.g. tetrahydrofuryl, morpholino, thiomorpholino, piperidino, pyrrolidino and piperazino), $C_{7-9}$ aralkyl groups, amino group, N-mono-$C_{1-4}$ alkylamino groups, N, N—di—$C_{1-4}$ alkylamino groups, $C_{2-8}$ acylamino groups (e.g. acetylamino, propionylamino and benzoylamino), amidino group, $C_{2-8}$ acyl group (e.g. $C_{2-8}$ alkanoyl groups), carbamoyl group, N-mono-$C_{1-4}$ alkyl carbamoyl groups, N,N—di—$C_{1-4}$ alkyl carbamoyl groups, sulfamoyl group, N-mono-$C_{1-4}$ alkyl sulfamoyl groups, N,N—di—$C_{1-4}$ alkyl sulfamoyl groups, carboxyl group, $C_{2-8}$ alkoxycarbonyl groups, hydroxyl group, $C_{1-4}$ alkoxy groups, $C_{2-5}$ alkenyloxy groups, $C_{3-7}$ cycloalkyloxy groups, $C_{7-9}$ aralkyloxy groups, $C_{6-14}$ aryloxy groups, mercapto group, $C_{1-4}$ alkylthio groups, $C_{7-9}$ aralkylthio groups $C_{6-14}$ arylthio groups, sulfo group, cyano group, azido group, nitro group, nitroso group and halogen atom.

In the formula (I), R is preferably an optionally substituted heterocyclic group. R is more preferably pyridyl, oxazolyl or thiazolyl group which is optionally substituted by 1 to 3 substituents selected from $C_{1-3}$ alkyl group, furyl group, thienyl group, phenyl group and naphthyl group.

R' in the formula (II) has the same definition as R except that R' does not represent benzopyranyl group when m and n are 0; X represents CH; A represents a bond; Q represents sulfur atom; $R^1$, L and M represent hydrogen atom; and ring E does not have further substituents.

In the formulae (I) and (II), Y represents —CO—, —CH(OH)— or —NR³— (wherein $R^3$ represents an optionally substituted alkyl group), preferably —CH(OH)— or —NR³—. As the alkyl group in the optionally substituted alkyl group represented by $R^3$, mention is made of, for example, $C_{1-4}$ alkyl groups such as methyl, ethyl, propyl, isopropyl, butyl, isobutyl, sec.-butyl and t.-butyl. Examples of the substituents include halogen (e.g., fluorine, chlorine, bromine and iodine), $C_{1-4}$ alkoxy groups (e.g. methoxy, ethoxy, propoxy, butoxy, isobutoxy, sec.-butoxy and t.-butoxy), hydroxyl group, nitro group and $C_{1-4}$ acyl groups (e.g. formyl, acetyl and propionyl).

The symbol m is 0 or 1, preferably 0.

The symbol n is 0, 1 or 2, preferably 0 or 1.

X represents CH or N, preferably CH.

In the formulae (I) and (II), A represents a bond or a $C_{1-7}$ divalent aliphatic hydrocarbon group. The aliphatic hydrocarbon group may be straight-chain or branched, and saturated or unsaturated. Specific examples of the aliphatic hydrocarbon group include saturated ones [e.g. —CH₂—, —CH(CH₃)—, —(CH₂)₂—, —CH(C₂H₅)—, —(CH₂)₃—, —(CH₂)₄—, —(CH₂)₅—, —(CH₂)₆— and —(CH₂)₇—] and unsaturated ones [e.g. —CH=CH—, —C(CH₃)=CH—, —CH=CH—CH₂—, —C(C₂H₅)=CH—, —CH₂—CH=CH—CH₂—, —CH₂—CH₂—CH=CH—CH₂—. —CH=CH—CH=CH—CH₂— and —CH=CH—CH=CH—CH=CH—CH₂—. A is preferably a bond or $C_{1-4}$ divalent aliphatic hydrocarbon groups, the aliphatic hydrocarbon groups preferably being saturated. A is more preferably a bond or —(CH₂)₂—.

As the alkyl group represented by $R^1$, substantially the same one as the alkyl group in the above-mentioned $R^3$. $R^1$ is preferably hydrogen atom.

In the formulae (I) and (II), the partial formula:

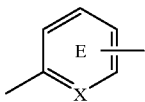 preferably represents the formula: 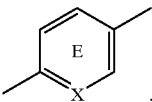

Ring E has 1 to 4 substituents at any substitutable positions. Examples of such substituents include alkyl group, optionally substituted hydroxyl group, halogen atom, optionally substituted acyl group and optionally substituted amino group. These substituents have substantially the same meaning as those described as substituents of the hydrocarbon group and heterocyclic group represented by R.

Ring E, namely the partial formula:

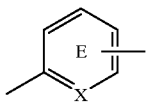 preferably represents the formula: 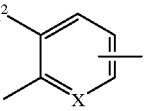

wherein $R^2$ represents hydrogen atom, an alkyl group, an optionally substituted hydroxyl group, a halogen atom, an optionally substituted acyl group, nitro group or an optionally substituted amino group.

As the alkyl group, optionally substituted hydroxyl group, halogen atom, optionally substituted acyl group and optionally substituted amino group represented by $R^2$, mention is made of those described as substituents of the hydrocarbon group and heterocyclic group represented by R. $R^2$ is preferably hydrogen atom, optionally substituted hydroxyl group or halogen atom, more preferably hydrogen atom or optionally substituted hydroxyl group, especially preferably hydrogen atom or $C_{1-4}$ alkoxy groups.

In the formulae (I) and (II), L and M represent hydrogen atom, or they may optionally be combined with each other to form a bond. L and M are preferably hydrogen atom.

In the compounds wherein L and M are combined with each other to form a bond, there exist (E)- and (Z)- isomers relative to the double bond at the 5-position of the azolidinedione ring.

And, in the compounds wherein L and M respectively represent hydrogen atom, there exist (R)- and (S)- optical isomers due to the asymmetric carbon at the 5-position of the azolidinedione ring. The compounds include these (R)- and (S)- optical isomers and racemic isomers.

Preferable examples of the compounds represented by the formula (I) or (II) includes those in which R is pyridyl, oxazolyl or thiazolyl group optionally having 1 to 3 substituents selected from $C_{1-3}$ alkyl, furyl, thienyl, phenyl and naphthyl; m is 0; n is 0 or 1; X is CH; A is a bond or —$(CH_2)_2$—; $R^1$ is hydrogen atom; ring E, namely the partial formula:

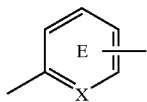 represents the formula: 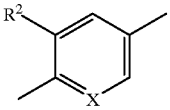

and $R^2$ is hydrogen atom or $C_{1-4}$ alkoxy group; and L and M are both hydrogen atom.

Preferable examples of the compound represented by the formula (I) include (1) the compound represented by the formula (III) such as 5-[4-[2-(3-ethyl-2-pyridyl)ethoxy]benzyl]-2,4-thiazolidinedione; 5-[4-[2-(4-ethyl-2-pyridyl)ethoxy]-benzyl]-2,4-thiazolidinedione; 5-[4-[2-(5-ethyl-2-pyridyl)ethoxy]benzyl]-2,4-thiazolidinedione (generic name: pioglitazone); and 5-[4-[2-(6-ethyl-2-pyridyl)-ethoxy]benzyl]-2,4-thiazolidinedione;

(2) (R)-(+)-5-[3-[4-[2-(2-furyl)-5-methyl-4-oxazolylmethoxy]-3-methoxyphenyl]propyl]-2,4-oxazolidinedione; and (3) 5-[[4-[(3,4-dihydro-6-hydroxy-2,5,7,8-tetramethyl-2H-1-benzopyran-2-yl)methoxy]phenyl]methyl]-2,4-thiazolidinedione (generic name: troglitazone/CS-045).

The compound represented by the formula (I) is especially preferably pioglitazone.

The compound represented by the formula (II) is preferably the compound represented by the formula (III) and (R)-(+)-5-[3-[4-[2-(2-furyl)-5-methyl-4-oxazolylmethoxy]-3-methoxyphenyl]propyl]-2,4-oxazolidinedione, more preferably pioglitazone.

The pharmacologically acceptable salt of the compound represented by the formula (I) or (II) are exemplified by salts with inorganic bases, salts with organic bases, salts with inorganic acids, salts with organic acids, and salts with basic or acidic amino acids.

Preferable examples of salts with inorganic bases include salts with alkali metals such as sodium, potassium, etc., salts with alkaline earth metals such as calcium, magnesium, etc., and salts with aluminum, ammonium, etc.

Preferable examples of salts with organic bases include salts with trimethylamine, triethylamine, pyridine, picoline, ethanolamine, diethanolamine, triethanolamine, dicyclohexylamine, N,N-dibenzylethylenediamine, etc.

Preferable examples of salts with inorganic acids include salts with hydrochloric acid, hydrobromic acid, nitric acid, sulfuric acid, phosphoric acid, etc.

Preferable examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferable examples of salts with basic amino acids include salts with arginine, lysine, ornithine, etc., and preferable examples of salts with acidic amino acids include salts with aspartic acid, glutamic acid, etc.

The pharmacologically acceptable salt of the compound represented by the formula (III) is preferably a salt with an inorganic acid, more preferably a salt with hydrochloric acid. Especially, pioglitazone is preferably used in the form of salt with hydrochloric acid.

The compounds represented by the formula (I) or (II) or a salt thereof can be produced in accordance with, for example, methods described in JPA S55(1980)-22636(EP-A 8203), JPA S60(1985)-208980(EP-A 155845), JPA S61(1986)-286376(EP-A 208420), JPA S61(1986)-85372(EP-A 177353), JPA S61(1986)-267580(EP-A 193256), JPA H5(1993)-86057(WO 92/18501), JPA H7(1995)-82269 (EP-A 605228), JPA H7(1995)-101945(EP-A 612743), EP-A 643050, EP-A 710659, etc. or methods analogous thereto.

Insulin sensitivity enhancers include 5-[[3,4-dihydro-2-(phenylmethyl)-2H-1-benzopyran-6yl]methyl]-2,4-thiazolidinedione (generic name: englitazone) or its sodium salt;

5-[[4-[3-(5-methyl-2-phenyl-4-oxazolyl)-1-oxopropyl]phenyl]methyl]-2,4-thiazolidinedione (generic name: darglitazone/CP-86325) or its sodium salt;

5-[2-(5-methyl-2-phenyl-4-oxazolylmethyl)benzofuran-5-ylmethyl]-2,4-oxazolidinedione (CP-92768);

5-(2-naphthalenylsulfonyl)-2,4-thiazolidinedione (AY-31637);

4-[(2-naphthalenyl)methyl]-3H-1,2,3,5-oxathiadiazol-2-oxide (AY-30711); and

5-[[4-[2-(methyl-2-pyridylamino)ethoxy]phenyl]-methyl]-2,4-thiazolidinedione (BRL-49653), etc. in addition to compounds mentioned hereinbefore.

In the present invention, examples of the drug which is used in combination with the above-mentioned insulin sensitivity enhancer include an α-glucosidase inhibitor, an aldose reductase inhibitor, a biguanide, a statin compound, a squalene synthesis inhibitor, a fibrate compound, a LDL catabolism enhancer and an angiotensin converting enzyme inhibitor.

α-Glucosidase inhibitors are drugs which inhibit digestive enzymes such as amylase, maltase, α-dextrinase, sucrase, etc. to retard digestion of starch and sugars. Examples of the α-glucosidase inhibitors include acarbose, N-(1,3-dihydroxy-2-propyl)valiolamine (generic name; voglibose), miglitol, etc. with preferance given to voglibose.

Aldose reductase inhibitors are drugs which inhibit the first-stage rate-limitting enzyme in the polyol pathway to prevent or arrest diabetic complications. In the hyperglycemic state of diabetes, the utilization of glucose in the polyol pathway is increased and the excess sorbitol accumulated intracellularly as a consequence acts as a tissue toxin and hence evokes the onset of complications such as diabetic neuropathy, retinopathy, and nephropathy. Examples of the aldose reductase inhibitors include tolurestat; epalrestat; 3,4-dihydro-2,8-diisopropyl-3-thioxo-2H-1,4-benzoxazine-4-acetic acid; 2,7-difluoro-spiro(9H-fluorene-9,4'-imidazolidine)-2',5'-dione (generic name: imirestat);

3-[(4-bromo-2-fluorophenyl)methyl]-7-chloro-3,4-dihydro-2,4-dioxo-1(2H)-quinazoline acetic acid (generic name: zenarestat);

6-fluoro-2,3-dihydro-2',5'-dioxo-spiro[4H-1-benzopyran-4,4'-imidazolidine]-2-carboxamide (SNK-860); zopolrestat; sorbinil; and 1-[(3-bromo-2-benzofuranyl)sulfonyl]-2,4-imidazolidinedione (M-16209), etc.

Biguanides are drugs having actions of stimulation of anaerobic glycolysis, increase of the sensitivity to insulin in the peripheral tissues, inhibition of glucose absorption from the intestine, suppression of hepatic gluconeogenesis, and inhibition of fatty acid oxidation. Examples of the biguanides include phenformin, metformin, buformin etc.

Statin compounds are drugs having actions of lowering blood cholesterol levels by inhibiting hydroxymethylglutalyl CoA (HMG—CoA) reductase. Examples of the statin compounds include pravastatin and its sodium salt, simvastatin, lovastatin, atorvastatin, fluvastatin, etc.

Squalene synthesis inhibitors are drugs having actions of lowering blood cholesterol levels by inhibiting synthesis of squalene. Examples of the squalene synthesis inhibitors include (S)-α-[Bis[2,2-dimethyl-1-oxopropoxy)methoxy] phosphinyl]-3-phenoxybenzenebutanesulfonic acid, mono potassium salt (BMS-188494).

Fibrate compounds are drugs having actions of lowering blood cholesterol levels by inhibiting synthesis and secretion of triglycerides in liver and activating a lipoprotein lipase.

Examples of the fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, etc.

LDL catabolism enhancers are drugs having actions of lowering blood cholesterol levels by increasing the number of LDL (low-density lipoprotein) receptors.

Examples of the LDL catabolism enhancers include the compound which is described in JPA H7(1995)-316144 and represented by the formula:

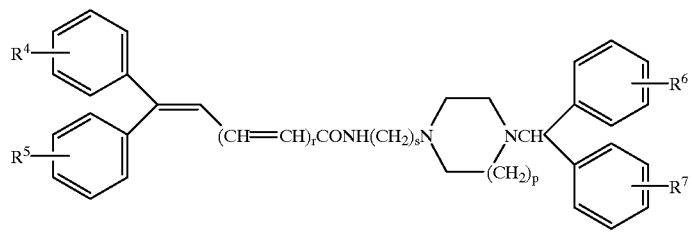

wherein $R^4$, $R^5$, $R^6$ and $R^7$ are the same or different, and represent hydrogen atom, a halogen atom, a lower alkyl group or a lower alkoxy group; r is 0–2; s is 2–4; p is 1–2; or a salt thereof; specifically N-[2-[4-bis(4-fluorophenyl) methyl-1-piperazinyl]ethyl]-7,7-diphenyl-2,4,6-heptatrienic acid amide, etc.

The above-mentioned statin compounds, squalene synthesis inhibitors, fibrate compounds and LDL catabolism enhancers can be substituted with other drugs having the property to lower blood cholesterol and triglyceride levels. Examples of these drugs include nicotinic acid derivatives such as nicomol and niceritrol; antioxidants such as probucol; and ion-exchange resins such as colestyramin.

Angiotensin converting enzyme inhibitors are drugs having actions of partially lowering blood glucose levels as well as lowering blood pressure by inhibiting angiotensin converting enzymes. Examples of the angiotensin converting enzyme inhibitors include captopril, enalapril, alacepril, delapril, ramipril, lisinopril, imidapril, benazepril, ceronapril, cilazapril, enalaprilat, fosinopril, moveltopril, perindopril, quinapril, spirapril, temocapril, trandolapril, etc.

In the present invention, especially preferred is the pharmaceutical composition which comprises an insulin sensitivity enhancer in combination with an α-glucosidase inhibitor. The insulin sensitivity enhancer is especially preferably pioglitazone, and the α-glucosidase inhibitor is especially preferably voglibose.

In the present invention, examples of the drug which is used in combination with the compound represented by the formula (II) or a pharmacologically acceptable salt thereof include an insulin secretion enhancer and/or an insulin preparation.

Insulin secretion enhancers are drugs having the property to promote secretion of insulin from pancreatic β cells. Examples of the insulin secretion enhancers include sulfonylureas (SU). The sulfonylureas (SU) are drugs which promote secretion of insulin from pancreatic β cells by transmitting signals of insulin secretion via SU receptors in the cell membranes. Examples of the SU include tolbutamide; chlorpropamide; tolazamide; acetohexamide; 4-chloro-N-[(1-pyrolidinylamino)carbonyl]-benzenesulfonamide (generic name: glycopyramide) or its ammonium salt; glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; tolcyclamide, etc.

Insulin secretion enhancers include N-{[4-(1-methylethyl)cyclohexyl)carbonyl]-D-phenylalanine (AY-4166); calcium (2S)-2-benzyl-3-(cis-hexahydro-2-isoindolinylcarbonyl)propionate dihydrate (KAD-1229); and glimepiride (Hoe 490), etc. in addition to compounds mentioned hereinbefore. The insulin secretion enhancer is especially preferably glibenclamide.

Examples of the insulin preparations include animal insulin preparations typically extracted from bovine or porcine pancreas and human insulin preparations synthesized by genetic engineering techniques typically using *Escherichia coli* or yeasts. While insulin preparations are available in a variety of types, e.g. immediate-acting, bimodal-acting, intermediate-acting, and long-acting, these type of preparations can be selectively administered according to the patient's condition.

In the present invention, especially preferred is the pharmaceutical composition which comprises the compound represented by the formula (II) or a pharmacologically acceptable salt thereof in combination with an insulin secretion enhancer. The compound represented by the formula (II) or a pharmacologically acceptable salt thereof is especially preferably pioglitazone, and the insulin secretion enhancer is especially preferably glibenclamide.

The pharmaceutical composition comprising an insulin sensitivity enhancer in combination with at least one member selected from the group consisting of an α-glucosidase inhibitor, an aldose reductase inhibitor, a biguanide, a statin compound, a squalene synthesis inhibitor, a fibrate compound, a LDL catabolism enhancer and an angiotensin converting enzyme inhibitor; and the pharmaceutical composition comprising the compound represented by the formula (II) or a pharmacologically acceptable salt thereof in combination with an insulin secretion enhancer and/or an insulin preparation, both provided in accordance with the present invention, can be respectively put to use by mixing the respective active components either all together or independently with a physiologically acceptable carrier, excipient, binder, diluent, etc. and administering the mixture or mixtures either orally or non-orally as a pharmaceutical composition. When the active components are formulated independently, the respective formulations can be extemporaneously admixed using a diluent or the like and administered or can be administered independently of each other, either concurrently or at staggered times to the same subject.

The dosage form for said pharmaceutical composition includes such oral dosage forms as granules, powders, tablets, capsules, syrups, emulsions, suspensions, etc. and such non-oral dosage forms as injections (e.g. subcutaneous, intravenous, intramuscular and intraperitoneal injections), drip infusions, external application forms (e.g. nasal spray preparations, transdermal preparations, ointments, etc.), and suppositories (e.g. rectal and vaginal suppositories).

These dosage forms can be manufactured by the per se known technique conventionally used in pharmaceutical procedures. The specific manufacturing procedures are as follows.

To manufacture an oral dosage form, an excipient (e.g. lactose, sucrose, starch, mannitol, etc.), a dis-integrator (e.g. calcium carbonate, carboxymethylcellulose calcium, etc.), a binder (e.g. α-starch, gum arabic, carboxymethylcellulose, polyvinylpyrrolidone, hydroxypropylcellulose, etc.), and a lubricant (e.g. talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethyl-cellulose, hydroxymethylcellulose, polyoxyethylene glycol, cellulose acetate phthalate, hydroxypropylmethylcellulose phthalate, and Eudragit (Rohm & Haas, Germany, methacrylic-acrylic copolymer).

Injections can be manufactured typically by the following procedures. The active component or components are dissolved, suspended or emulsified in an aqueous vehicle (e.g. distilled water, physiological saline, Ringer's solution, etc.) or an oily vehicle (e.g. vegetable oil such as olive oil, sesame oil, cottonseed oil, corn oil, etc. or propylene glycol) together with a dispersant (e.g. Tween 80 (Atlas Powder, U.S.A.), HCO 60 (Nikko Chemicals), polyethylene glycol, carboxymethylcellulose, sodium alginate, etc.), a preservative (e.g. methyl p-hydroxybenzoate, propyl p-hydroxybenzoate, benzyl alcohol, chlorobutanol, phenol, etc.), an isotonizing agent (e.g. sodium chloride, glycerol, sorbitol, glucose, inverted sugar, etc.) and other additives. If desired, a solubilizer (e.g. sodium salicylate, sodium acetate, etc.), a stabilizer (e.g. human serum albumin), a soothing agent (e.g. benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g. lactose, mannitol, starch, microcrystalline cellulose, sucrose, etc.), a thickener (e.g. natural gums, cellulose derivatives, acrylic polymers, etc.), etc., are processed into powders. The liquid composition can be manufactured in substantially the same manner as the injections mentioned above. The semi-solid composition is preferably provided in a hydrous or oil gel form or an ointment form. These compositions may optionally contain a pH control agent (e.g. carbonic acid, phosphoric acid, citric acid, hydrochloric acid, sodium hydroxide, etc.), and a preservative (e.g. p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g. cacao butter, Witepsols (Dinamit-Nobel), etc.], medium-chain fatty acids [e.g. Migriols (Dinamit-Nobel), etc.], vegetable oils (e.g. sesame oil, soybean oil, cottonseed oil, etc.), etc. The water-soluble base includes, for instance, polyethylene glycols, propylene glycol, etc. The hydrophilic base includes, for instance, natural gums, cellulose derivatives, vinyl polymers, and acrylic polymers, etc.

The pharmaceutical composition of the present invention is low in toxicity and can be safely used in mammals (e.g. humans, mice, rats, rabbits, dogs, cats, bovines, horses, swines, monkeys).

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges. The preferred frequency of administration is 1 to 3 times a day.

The proportions of the active components in the pharmaceutical composition of the present invention can be appropriately selected according to the recipient, the recipient's age and body weight, current clinical status, administration time, dosage form, method of administration, and combination of active components, among other factors. When, for example, the compound represented by the formula (I) or a pharmacologically acceptable salt thereof (e.g. pioglitazone) which is the insulin sensitivity enhancer and voglibose which is an α-glucosidase inhibitor are to be administered in combination to a human subject, voglibose is used in a proportion of usually about 0.0001 to 0.2 weight parts and preferably about 0.001 to 0.02 weight parts relative to 1 weight part of the compound or a salt thereof. When, for example, the compound represented by the formula (II) or a pharmacologically acceptable salt thereof and glibenclamide which is an insulin secretion enhancer are to be administered in combination to a human subject, glibenclamide is used in a proportion of usually about 0.002 to 5 weight parts and preferably about 0.025 to 0.5 weight parts, relative to 1 weight part of the compound or a pharmacologically acceptable salt thereof.

The pharmaceutical composition of the present invention shows a marked synergistic effect compared with administration of either active component alone. For example, compared with cases in which each of these active components was administered to diabetic Wistar fatty rats with genetical obesity, administration of these active components in combination resulted in marked improvements in both hypoglycemia and reduced glucose tolerance. Thus, the pharmaceutical composition of the present invention lowers blood glucose in diabetics more effectively than it is the case with administration of each component drug alone and, therefore, can be used advantageously for the prophylaxis and treatment of diabetic complications.

Furthermore, since the pharmaceutical composition of the present invention develops sufficient efficacy with reduced doses as compared with the administration of any one of the active components alone, the side effects of the respective components (e.g. gastrointestinal disorders such as diarrhea, etc.) can be reduced.

The following working examples and experimental examples are merely intended to illustrate the present invention in further detail but should by no means be construed as defining the scope of the invention.

The pharmaceutical composition of the present invention can be prepared according to the following formulations.

WORKING EXAMPLE 1

Capsules

| | |
|---|---:|
| (1) Pioglitazone hydrochloride | 30 mg |
| (2) Voglibose | 0.2 mg |
| (3) Lactose | 60 mg |
| (4) Microcrystalline cellulose | 79.8 mg |
| (5) Magnesium stearate | 10 mg |
| Total | 180 mg |

The whole amounts of (1), (2), (3) and (4) and half the amount of (5) are mixed well and granulated in the conventional manner. Then, the balance of (5) is added and, after mixing, the whole composition is filled in a gelatin hard capsule shell.

WORKING EXAMPLE 2

| | |
|---|---:|
| (1) Pioglitazone hydrochloride | 10 mg |
| (2) Glibenclamide | 1.25 mg |
| (3) Lactose | 86.25 mg |
| (4) Corn starch | 20 mg |
| (5) Polyethylene glycol | 2.5 mg |
| (6) Hydroxypropylcellulose | 4 mg |
| (7) Carmellose calcium | 5.5 mg |
| (8) Magnesium stearate | 0.5 mg |
| | 130 mg (per tablet) |

The whole amounts of (1), (2), (3), (4), and (5), ⅔ amounts of (6) and (7), and ½ amount of (8) are mixed well and granulated in the conventional manner. Then, the balances of (6), (7) and (8) are added to the granules, which is mixed well and the whole composition is compressed with a tablet machine. The adult dosage is 3 tablets/day, to be taken in 1 to 3 divided doses.

WORKING EXAMPLE 3

Capsules

| | |
|---|---:|
| (1) Pioglitazone hydrochloride | 10 mg |
| (2) Epalrestat | 50 mg |
| (3) Lactose | 55 mg |
| (4) Microcrystalline cellulose | 55 mg |
| (5) Magnesium stearate | 10 mg |
| Total | 180 mg |

The whole amounts of (1), (2), (3) and (4) and ½ amount of (5) are mixed well and granulated in the conventional manner. Then, the balance of (5) is added and the whole composition is filled in gelatin capsule shell. The adult dosage is 3 capsules/day, to be taken in 1 to 3 doses.

EXPERIMENTAL EXAMPLE 1

Effect of pioglitazone hydrochloride in combination with α-glucosidase inhibitor in genetically obese and diabetic Wistar fatty rats Male Wistar fatty rats aged 14–19 weeks were divided into 4 groups of 5–6, and pioglitazone hydrochloride (1 mg/kg body wt./day, p.o.) and/or voglibose (an α-glucosidase inhibitor) (0.31 mg/kg body wt./day; administered by mixing in commercial diet at a rate of 5 ppm) was administered for 14 days. The blood was then collected from the tail vein and the plasma glucose and hemoglobin $A_1$ were determined by the enzymatic method (Encore Chemical System, Baker) and using a commercial kit (NC-ROPET, Nippon Chemiphar Co.), respectively. The results were expressed in mean±standard deviation for each group (n=5–6) and analyzed by Dunnett's test, which are shown in Table 1. The 1% level of significance was used.

TABLE 1

| Group | Plasma glucose (mg/dl) | Hemoglobin $A_1$ (%) |
| --- | --- | --- |
| Control | 345 ± 29 | 5.7 ± 0.4 |
| Pioglitazone | 215 ± 50* | 5.2 ± 0.3 |
| Voglibose | 326 ± 46 | 6.0 ± 0.6 |
| Pioglitazone + voglibose | 114 ± 23* | 4.5 ± 0.4* |

*P < 0.01 vs. control group

It is apparent from Table 1 that both the blood glucose and hemoglobin $A_1$ levels were remarkably lowered by combined administration of pioglitazone and voglibose as compared with the administration of either drug alone.

EXPERIMENTAL EXAMPLE 2

Effect of pioglitazone hydrochloride in combination with an insulin secretion enhancer in genetically obese and diabetic Wistar fatty rats Male Wistar fatty rats aged 13–14 weeks were divided into 4 groups of 5, and pioglitazone hydrochloride (3 mg/kg/day, p.o.) and/or glibenclamide (an insulin secretion enhancer) (3 mg/kg/day, p.o.) was administered for 7 days. Following an overnight fast, the oral glucose loading test (2 g glucose/kg/5 ml, p.o.) was carried out. Prior to glucose loading and 120 and 240 minutes after the loading, blood was collected from the tail vein and the plasma glucose was assayed by the enzymatic method (Encore Chemical System, Baker). The results were expressed in mean±SD for each group (n=5) and analyzed by Dunnett's test, which are shown in Table 2.

TABLE 2

| Group | Plasma glucose (mg/dl) | | |
| --- | --- | --- | --- |
| | 0 min. | 120 min. | 240 min. |
| Control | 119 ± 9 | 241 ± 58 | 137 ± 10 |
| Pioglitazone | 102 ± 12 | 136 ± 17* | 102 ± 19* |
| Glibenclamide | 118 ± 12 | 222 ± 61 | 106 ± 24* |
| Pioglitazone + glibenclamide | 108 ± 3 | 86 ± 10* | 60 ± 5* |

*P < 0.01 vs. control group

It is apparent from Table 2 that the increase of blood sugar following glucose loading was remarkably inhibited by the combined administration of pioglitazone and glibenclamide as compared with the administration of either drug alone.

The pharmaceutical composition of the present invention shows a potent depressive effect on diabetic hyperglycemia and is useful for prophylaxis and treatment of diabetes. Moreover, this pharmaceutical composition is useful for prophylaxis and treatment of diabetic complications such as diabetic neuropathy, nephropathy, retinopathy, macroangiopathy, and osteopenia. In addition, by appropriately selecting the kinds of component drugs, administration route, dosage, etc. according to clinical status, stable hypoglycemic efficacy in long-term therapy can be expected with an extremely low risk of side effect.

What is claimed is:

1. A method for reducing the side effects of active components administered to a diabetic patient, which comprises administering to said patient a therapeutically effective amount of an insulin sensitivity enhancer in combination with a biguanide as said active components.

2. The method according to claim 1, wherein the insulin sensitivity enhancer is a compound represented by the formula:

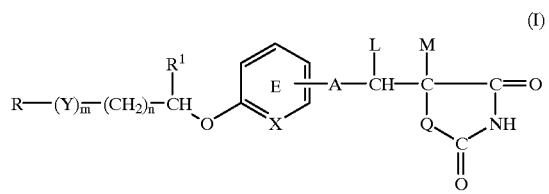

wherein R represents an optionally substituted hydrocarbon or heterocyclic group; Y represents a group represented by —CO—, —CH(OH)— or —$NR^3$— wherein $R^3$ represents an optionally substituted alkyl group; m is 0 or 1; n is 0, 1 or 2; X represents CH or N; A represents a bond or a $C_{1-7}$ divalent aliphatic hydrocarbon group; Q represents oxygen atom or sulfur atom; $R^1$ represents hydrogen atom or an alkyl group; ring E may optionally have 1 to 4 further substituents, and the substituents may optionally be combined with $R^1$ to form a ring; L and M respectively represent hydrogen atom, or L and M may optionally be combined with each other to form a bond; or a pharmacologically acceptable salt thereof.

3. The method according to claim 2, wherein R is an optionally substituted heterocyclic group.

4. The method according to claim 2, wherein m is 0.

5. The method according to claim 2, wherein X is CH.

6. The method according to claim 2, wherein $R^1$ is hydrogen atom.

7. The method according to claim 2, wherein the partial formula:

wherein $R^2$ represents hydrogen atom, an alkyl group, an optionally substituted hydroxyl group, a halogen atom, an optionally substituted acyl group, nitro group or an optionally substituted amino group.

8. The method according to claim 2, wherein L and M are hydrogen atoms.

9. The method according to claim 2, wherein R is pyridyl, oxadolyl or thiazolyl group optionally having 1 to 3 substituents selected from $C_{1-3}$ alkyl, furyl, thienyl, phenyl and naphthyl; m is 0; n is 0 or 1; X is CH; A is a bond or —$(CH_2)_2$—; $R^1$ is hydrogen atom; where in partial formula:

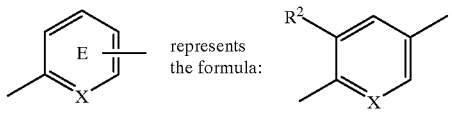 represents the formula: 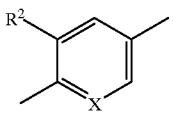

and wherein $R^2$ is hydrogen atom or $C_{1-4}$ alkoxy group; and L and M are both hydrogen atoms.

10. The method according to claim 2, wherein the compound represented by the formula (I) is pioglitazone or its hydrochloride.

11. The method according to claim 1, wherein the biguanide is selected from the group consisting of phenformin, metformin and buformin.

12. The method according to claim 1, wherein the biguanide is metformin.

13. The method according to claim 1, wherein the insulin sensitivity enhancer is pioglitazone or its hydrochloride and the biguanide is metformin.

14. The method according to claim 1, wherein the insulin sensitivity enhancer is troglitazone.

15. The method according to claim 1, wherein the insulin sensitivity enhancer is 5-[[4-[2-(methyl-2-pyridylamino) ethoxy]phenyl]-methyl]-2,4-thiazolidinedione or its pharmacologically acceptable salt.

16. The method according to claim 1, wherein the insulin sensitivity enhancer and biguanide are mixed together to form an admixture and the admixture is administered to the mammal.

17. The method according to claim 1, wherein the insulin sensitivity enhancer and biguanide are not mixed together but are administered independently to the mammal.

* * * * *

UNITED STATES PATENT AND TRADEMARK OFFICE
CERTIFICATE OF CORRECTION

PATENT NO.    : 6,172,090 B1
DATED         : January 9, 2001
INVENTOR(S)   : Hitoshi Ikeda et al.

Page 1 of 1

It is certified that error appears in the above-identified patent and that said Letters Patent is hereby corrected as shown below:

Column 18,
Line 64, change "oxadolyl" to -- oxazolyl --;
Line 67, change "where in" to -- wherein --.

Signed and Sealed this

Eighteenth Day of December, 2001

Attest:

JAMES E. ROGAN
*Attesting Officer*    *Director of the United States Patent and Trademark Office*